(12) United States Patent
Sanghvi et al.

(10) Patent No.: US 6,541,626 B2
(45) Date of Patent: Apr. 1, 2003

(54) PROCESS FOR SELECTIVE N-ACYLATION OF PURINE NUCLEOSIDES

(75) Inventors: Yogesh S. Sanghvi, Encinitas, CA (US); Krishna Misra, Allahabad (IN); Snehlata Tripathi, Allahabad (IN)

(73) Assignees: ISIS Pharmaceuticals, Inc., Carlsbad, CA (US); University of Allahabad (IN)

(*) Notice: Subject to any disclaimer, the term of this patent is extended or adjusted under 35 U.S.C. 154(b) by 0 days.

(21) Appl. No.: 09/836,127

(22) Filed: Apr. 17, 2001

(65) Prior Publication Data

US 2003/0022862 A1 Jan. 30, 2003

(51) Int. Cl.[7] .................. C07H 19/16; C07H 19/00; C07H 21/00; C07H 19/22
(52) U.S. Cl. .................. 536/27.22; 536/22.1; 536/27.1; 536/27.2; 536/27.21
(58) Field of Search ............ 536/27.22, 27.21, 536/27.2, 27.1, 22.1

(56) References Cited

U.S. PATENT DOCUMENTS

| 4,849,513 A | * | 7/1989 | Smith et al. | |
|---|---|---|---|---|
| 5,470,974 A | | 11/1995 | Summerton et al. | ........ 544/118 |
| 5,523,398 A | * | 6/1996 | Glasser et al. | |
| 5,616,700 A | * | 4/1997 | Reddy et al. | |
| 5,817,811 A | * | 10/1998 | Breipohl et al. | |

FOREIGN PATENT DOCUMENTS

WO    WO 00/08044    2/2000

OTHER PUBLICATIONS

U.S. patent application Ser. No. 09/378,568, Manoharan et al. filed Aug. 19, 1999.
Damha, M.J. et al., "Hybrids of RNA and Arabinonucleic Acids (ANA and 2'F–ANA) are Substrates of Ribonuclease H", *J. Am. Chem. Soc*, 1998, 120, 12976–12977.
Damha, M.J. et al., "Duplex Recognition by Oligonucleotides Containing 2'–Deoxy–2'–fluoro–D–arabinose and 2'–Deoxy–2'fluoro–D–ribose, Intermolecular 2'–OH–Phosphate Contacts versus Sugar Puckering in the Stabilization of Triple–Helical Complexes", *Bioconjugate Chem.*, 1999, 10, 299–305.
Damha, M.J. et al., "2'–Deoxy–2'– fluoro–beta–D–arabinonucleosides and Oligonucleotides (2'F–ANA): Synthesis and Physicochemical Studies", *Nucleic Acids Res.*, 2000, 28(18), 3625–3635.
Damha, M.J. et al., "Synthesis and Biophysical Properties of Arabinonucleic Acids (ANA): Circular Dichroic Spectra, Melting Temperatures, and Ribonuclease H Susceptibility of ANA–RNA Hybrid Duplexes", *Biochemistry*, 2000, 39(24), 7050–7062.
Iyer, *Current Protocols in Nucleic Acid Chemistry*, 2000, 2.17–2.19.
Pon, R.T., "Solid–Phase Supports for Oligonucleotide Synthesis", *Methods in Molecular Biology*, 20(19), 465–496.
Reese, C.B. et al., "The H–phosphonate Approach to the Solution Phase Synthesis of Linear and Cyclic Oligoribonucleotides", *Nucleic Acids Research*, 1999, 27(4), 963–971.
Reese, C.B. et al., "A New Approach to the Synthesis of Oligonucleotides and their Phosphorothioate Analogues in Solution" *Biorg. Med. Chem. Lett.*, 1997, 7, 2878–2792.
Schaller, H., et al., "Studies on polynucleotides. XXIV.[1] The stepwise synthesis of specific deoxyribopolynucleotides (4).[2] Protected derivatives of deoxyribonucleosides and new syntheses of deoxyribonucleoside–3' phosphates[3]," *J. Biol. Chem.*, 1963, 238(85), 3821–3927.
Ti, G.S., et al., "Transient protection: efficient one–flask syntheses of protected deoxynucleosides[1]," *J. Am. Chem. Soc.*, 1982, 104, 1316–1319.
Bodanszky, M., et al., "Peptide bond formation with the aid of coupling reagents," *The Practice of Peptide synthesis*, 2nd Ed., 1994, 118–126.
Bodanszky, M., et al., "Preparation of p–nitrophenyl esters," *The Practice of Peptide Synthesis*, 2nd Ed., 1994, 97–107.
Dorwald, F.Z., "Polystyrene," *Organic Synthesis on Solid Phase (Wiley–VCH)*, 2000, 15–16.

* cited by examiner

Primary Examiner—James O. Wilson
Assistant Examiner—Traviss C. McIntosh
(74) Attorney, Agent, or Firm—Woodcock Washburn LLP

(57) ABSTRACT

Methods for selectively protecting the exocyclic amino function of a purine nucleoside are provided using activating agents to effect acylation at the exocyclic amino site. Methods are also provided for recycling polymer bound coupling supports from the reaction mixtures produced upon N-acylation.

19 Claims, 1 Drawing Sheet

PROCESS FOR SELECTIVE N-ACYLATION OF PURINE NUCLEOSIDES

FIELD OF THE INVENTION

The present invention relates to methods for selectively protecting the exocyclic amino function of purine nucleosides.

BACKGROUND OF THE INVENTION

It is well known that most of the bodily states in mammals, including most disease states, are affected by proteins. Such proteins, either acting directly or through their enzymatic functions, contribute in major proportion to many diseases in animals and man. Classical therapeutics has generally focused on interactions with such proteins in efforts to moderate their disease causing or disease potentiating functions. Recently, however, attempts have been made to moderate the actual production of such proteins by interactions with molecules that direct their synthesis, such as intracellular RNA. By interfering with the production of proteins, it has been hoped to affect therapeutic results with maximum effect and minimal side effects. It is the general object of such therapeutic approaches to interfere with or otherwise modulate gene expression leading to undesired protein formation.

One method for inhibiting specific gene expression is the use of oligonucleotides and oligonucleotide analogs as "antisense" agents. The oligonucleotides or oligonucleotide analogs complimentary to a specific, target, messenger RNA (mRNA) sequence are used. Antisense methodology is often directed to the complementary hybridization of relatively short oligonucleotides and oligonucleotide analogs to single-stranded mRNA or single-stranded DNA such that the normal, essential functions of these intracellular nucleic acids are disrupted. Hybridization is the sequence specific hydrogen bonding of oligonucleotides or oligonucleotide analogs to Watson-Crick base pairs of RNA or single-stranded DNA. Such base pairs are said to be complementary to one another.

Oligonucleotides and oligonucleotide analogs are now accepted as therapeutic agents holding great promise for therapeutics and diagnostics methods. But applications of oligonucleotides and oligonucleotide analogs as antisense agents for therapeutic purposes, diagnostic purposes, and research reagents often require that the oligonucleotides or oligonucleotide analogs be synthesized in large quantities.

Three principal methods have been used for the synthesis of oligonucleotides. The phosphotriester method, as described by Reese, *Tetrahedron* 1978, 34, 3143; the phosphoramidite method, as described by Beaucage, in *Methods in Molecular Biology: Protocols for Oligonucleotides and Analogs;* Agrawal, ed.; Humana Press: Totowa, 1993, Vol. 20, 33–61; and the H-phosphonate method, as described by Froehler in *Methods in Molecular Biology: Protocols for Oligonucleotides and Analogs* Agrawal, ed.; Humana Press: Totowa, 1993, Vol. 20, 63–80.

The phosphotriester approach has been widely used for solution phase synthesis, whereas the phosphoramidite and H-phophonate strategies have found application mainly in solid phase syntheses. Recently, Reese reported a new approach to the solution phase synthesis of oligonucleotides on H-phosphonate coupling. See, Reese et al. *Nucleic Acids Research,* 1999, 27, 963–971, and Reese et al. *Biorg. Med. Chem. Lett.* 1997, 7, 2787–2792.

The synthesis of oligonucleotides requires the rapid and quantitative coupling of building blocks, such as nucleosides. Protecting groups are routinely used during these coupling reactions to allow selective reaction between two functional groups while protecting all other functionalities present in the reacting molecules. One such functional group that requires protection is the exocyclic amino function of a nucleobase. Amino protection helps to achieve quantitative coupling by inhibiting the risk of depurination of a growing oligonucleotide, which is facilitated under acidic conditions. In a partially depurinated oligomer chain, cleavage takes place at the site of depurination through double β-elimination, thereby generating truncated sequences.

Amino protecting groups, or N-acyl groups, are typically derived from carboxylic acids, which are used to acylate the amino functions, thereby forming amide bonds. Prior to the present invention, the methods used to acylate or protect the amino functions resulted in acylation of the hydroxyl functions present on the nucleoside as well. These methods involve various protection/deprotection steps resulting in decreased yields and increased product impurities. For example, the classical procedure used to protect amino groups on nucleosides involves per-acylatation of the nucleosides. The per-acylated nucleoside is then selectively hydrolyzed at the esters leaving the N-acylated nucleosides. See, Schaller, et al. *J. Am. Chem. Soc.* 1963, 85, 3821. According to another general procedure, the hydroxyl functions are first protected by silylating the groups prior to acylating the amino function. See, Ti et al. *J. Am. Chem. Soc.* 1982, 104, 1316. These groups must then be removed from the hydroxyl functions.

Another problem with conventional methods for protecting amino functions is that all the reagents used for protection are either in chloride or anhydride form. The preparation of acid chlorides from their respective acids is only about 50% and harmful chlorinating agents are required, such as $POCl_3$ and $SO_2Cl_2$. Additionally, these methods require a heating step which further increases costs for large-scale production.

In the last few years the use of antisense oligonucleotides has emerged as an exciting new therapeutic paradigm. As a result, very large quantities of therapeutically useful oligonucleotides are required in the near future. In view of the considerable expense and time required for synthesis of oligonucleotide building blocks, there has been a longstanding effort to develop successful methodologies for the preparation of oligonucleotides with increased efficiency and product purity.

SUMMARY OF THE INVENTION

According to one embodiment of the present invention, methods are provided for selectively protecting the exocyclic amino function of a nucleoside without compromising the hydroxyl groups of the sugar moieties. The methods comprise contacting an amino protecting reagent with an activating agent in the presence of a coupling agent to form an activated ester and reacting the activated ester with the purine nucleoside for a time and under conditions effective to covalently attach a protecting group onto the exocyclic amino function of the nucleoside.

In some embodiments of the present invention, the protecting group is formyl, isobutyryl, methoxyacetyl, allyloxycarbonyl, isopropoxyacetyl, levulinyl, 4-pentenoyl, 4-nitrophenylethyloxycarbonyl, phenyl acetyl, (4-t-butylphenyl)acetyl, 9-fluorenylmethoxycarbonyl, α-phenylcinnamoyl, phenoxyacetyl, 2-chlorophenoxyacetyl, 2-chloro-4-(tert-butyl) phenoxyacetyl, 4-(t-butyl)phenoxyacetyl, benzoyl, 4-methoxybenzoyl, 4-chlorobenzoyl, 4-nitrobenzoyl, 4-dimethylaminobenzoyl, 4-t-butylbenzoyl, 2-(methyl)sulfonylethoxycarbonyl, 2-(4-chloro)sulfonylethoxycarbonyl, 2-(4-nitro)sulfonylethoxycarbonyl, diphenylacetyl, 3,4-dichlorobenzoyl, 3-methoxy-4-phenoxybenzoyl, 2-(acetoxymethyl)benzoyl, benzoyloxymethylbenzoyl, 1,8-naphthaloyl, or 2-(t-butyldiphenylsilyloxymethyl)benzoyl. Other amino protecting groups are amenable to the present invention and within the purview of the skilled artisan.

Activating agents include, among others, O-nitrophenol, 2,4-dinitrophenol, 2,4,5-trichlorophenol, pentachlorophenol, N-hydroxyphthalimide, N-hydroxysuccinimide, N-hydroxyphthalimide, hydroxypiperidine, 5-chloro-8-hydroxy-quinoline, and compounds having one of the following formulae:

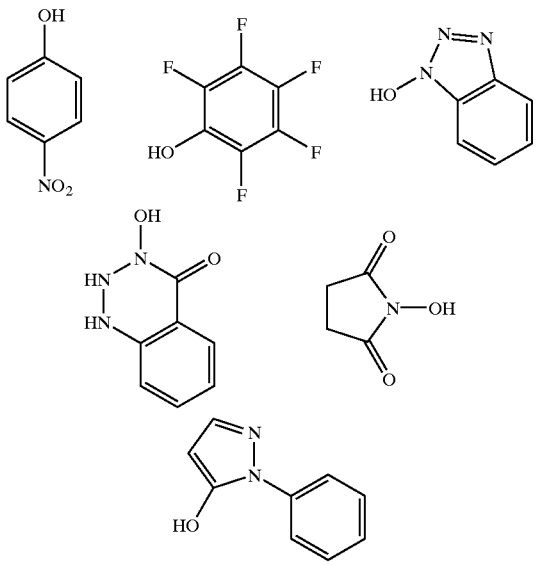

According to one embodiment of the present invention, methods are provided for recycling a polymer bound coupling agent from the reaction mixture containing the N-protected nucleoside prepared according to the methods described herein. Upon N-acylation, the reacted polymer bound coupling agent is filtered from the reaction mixture and recycled. The recycling is effected by dehydrating the polymer support with a dehydrating agent such as tosyl chloride or POCl₃ in the presence of an organic solvent for a time and under conditions effective to form the desired polymer bound coupling agent, which is ready for reuse.

BRIEF DESCRIPTION OF THE DRAWINGS

The numerous objects and advantages of the present invention may be better understood by those skilled in the art by reference to the accompanying detailed description and the following drawing, in which.

Figure 1:
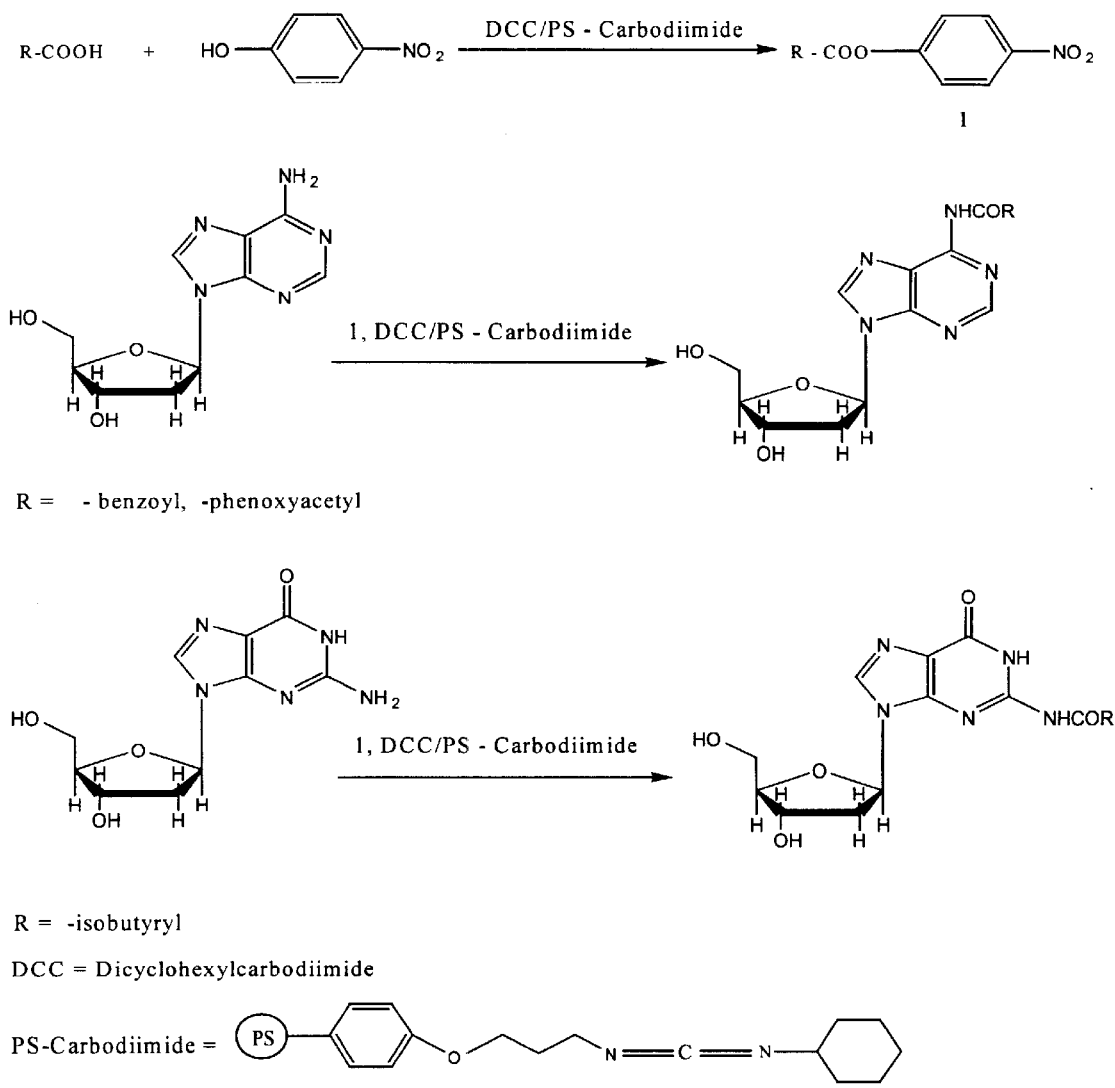
FIG. 1 shows the general method for N-protection of adenosine and guanosine.

The high selectivity achieved in protecting the exocyclic amino functions of nucleosides by the methods of the present invention is of great importance as it eliminates the need for the two-step procedures required by conventional methods. In addition, the methods of the present invention enhance product purity by providing crystalline compounds which can easily be purified using standard wet chemistry, thereby minimizing the need for chromatography. As greater efficiency is realized for oligonucleotide synthesis, large-scale production becomes more commercially viable resulting in the production of oligonucleotides that is sufficient to meet the growing demand.

According to one embodiment of the present invention, an amino protecting reagent is dissolved in an anhydrous organic solvent, such as dry dioxane, EtOAc, THF, Et₂O, or pyridine and contacted with an activating agent, such as p-nitrophenol, which is also dissolved in anhydrous organic solvent, in the presence of a coupling agent to form an activated ester (1), according to Scheme I, for example.

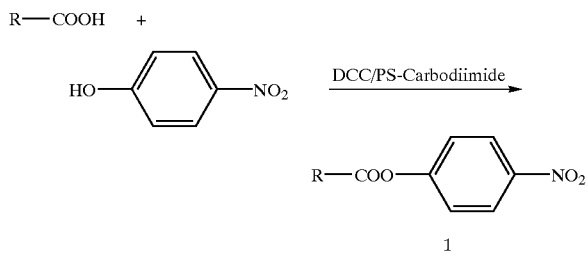

The reaction mixture is cooled to 0° C. in an ice-bath. The desired nucleoside is dissolved in an organic solvent, such as pyridine, and added gradually to the reaction mixture containing the activated ester as shown Scheme II, for example. After 10 minutes, the coupling agent is added again and the reaction mixture is stirred for 2 hours. The reaction mixture is filtered to remove precipitated DCU and evaporated to a gum in vacuo. The desired product (3) is extracted with organic solvent and the organic layer is dried over Na₂SO₄, filtered, and evaporated to dryness.

Scheme II

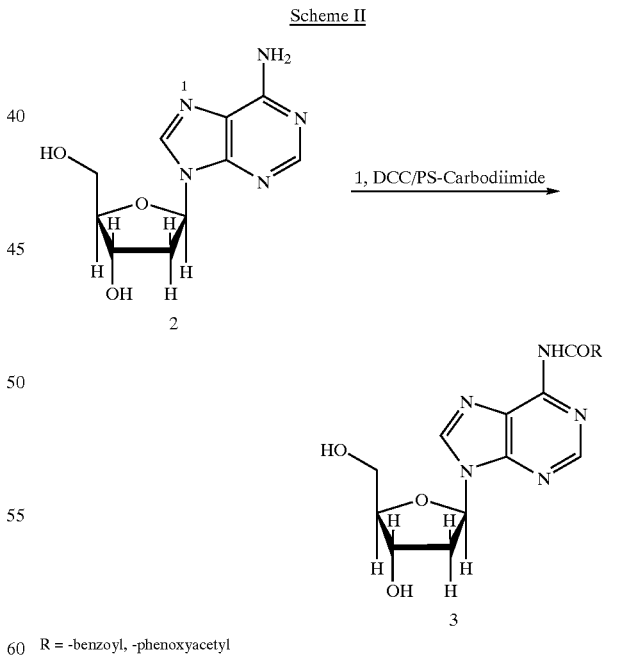

R = -benzoyl, -phenoxyacetyl

The acylation reactions may be catalyzed using any one of a number of different catalysts, such as those used to catalyze esterification reactions in peptide synthesis. See, Bodanszky and Bodanszky, *The Practice of Peptide Synthesis*, p. 155–117 (2nd Ed. 1994). For example, the reactions may be catalyzed with imidazole, 1-hydroxybenzotriazole, or 3-hydroxy-3,4-dihydro-quinazoline-4-one.

When DCC is used as the coupling agent, contamination with DCU exists which should be minimized. To assess the reaction conditions necessary to provide maximum yield and minimum contamination by DCU, a number of molar ratios at the nucleoside protection step for substrate to DCC have been attempted. For example, referring to Table 1 below, benzoyl protection of the exocyclic amino function of 2'-deoxyadenosine is illustrated using 1:1, 1:1.25:1:1.5 and 1:2 ratios, respectively. Using a 1:1 ratio, contamination with DCU is at a minimum but the yield is poor, i.e. approximately 50%. A ratio of 1:1.25 is optimum resulting in an 80% yield with a minimum level of contamination. This ratio has been successfully applied to other protecting groups, e.g. -phenoxyacetyl and -isobutyryl.

TABLE 1

Synthesis of $N^6$-Bz-dA
(% yield at different molar ratios of DCC to reactants

| Molar ratio at Activation step (ester formation) Acid (1):DCC | % yield (2) | Molar ratio at Nucleoside protection step ester:DCC | % yield (3) |
| --- | --- | --- | --- |
| 1:1 | 50 | 1:1 | 50 |
| 1:1.25 | 65 | 1:1.25 | 80 |
| 1:1.5 | 78* | 1:1.5 | 82* |
| 1:1.75 | 85¹ | 1:1.75 | 86¹ |
| 1:2 | 92¹¹ | 1:2 | 94¹¹ |

Benzoic acid (1) + p-nitrophenol→Benzoic p-nitrophenyl ester (2)→$N^6$-Benzoyl dA (3)
FAB-MS for ester 2: (*m/z 242, ¹m/z 241, ¹¹m/z 242)
FAB-MS for protected nucleoside 3: (*m/z 350, ¹m/z 351, ¹¹m/z 348)

The use of polymer bound coupling agents, such as PS-carbodiimide, as shown in Schemes I and II, results in enhanced yields and simplified purification procedures. The polymer supported coupling agent in its urea form is easily filtered from the reaction mixture. An additional advantage is provided in that the used polymer support may be recycled to retrieve the DCC form, which is ready for reuse. PS-carbodiimide is recovered by reacting the used polymer support (DCU derivatized polymer support) with a dehydrating agent in an organic solvent. Preferred dehydrating agents include $POCl_3$ and tosylchloride. Preferred organic solvents are $CH_2Cl_2$, $CHCl_3$, hexane, or pyridine. A list of additional solvents that are amenable to the present invention are described by Dorwald in *Organic Synthesis on Solid Phase*, p. 15 Wiley-VCH (2000), the disclosure of which is herein incorporated by reference.

Amino protecting groups that are amenable to the present invention include those described by Iyer, *Current Protocols in Nucleic Acid Chemistry*, 2.1.7–2.1.9 (2000), the disclosure of which is herein incorporated by reference. These groups appear in Table 2 below:

TABLE 2

Suitable Protecting Groups for Various Purine Nucleobases

| G (N2) | 7-deaza-6-methyl-G (N2) | G (N2); A (N6) |
| --- | --- | --- |
| Isobutyryl | Formyl | Allyloxycarbonyl |
| Methoxyacetyl | | Isopropoxyacetyl |
| phenylacetyl | | Levulinyl |

TABLE 2-continued

Suitable Protecting Groups for Various Purine Nucleobases

| G (N2) | 7-deaza-6-methyl-G (N2) | G (N2); A (N6) |
| --- | --- | --- |
| 4-tert-butylphenylacetyl | | 4-pentenoyl |
| Diphenylacetyl | | 4-nitrophenylethyloxycarbonyl |
| 3,4-dichlorobenzoyl | | 9-fluroenylmethoxycarbony |
| | | α-phenylcinnamoyl |
| | | phenoxyacetyl or 2-chlorophenoxyacetyl |
| | | 4-(tert-butyl)phenoxyacetyl |
| | | 4-R-phenylacetyl and R is H, OMe, Cl, $NO_2$, $NMe_2$, or $CMe_3$ |

The choice of nucleobase protecting groups depends on a variety of considerations. Most N-acyl protecting groups are stable in neutral or acidic medium and moderately stable at high pH (pH>13). As described by Iyer, a salient feature of N-acyl protecting groups is that their stability in alkaline pH can be modulated by the steric and electronic characteristics of specific acyl groups. Importantly, the stability of the acyl function towards alkaline hydrolysis is determined by the nature of the heterocyclic base. For example, the rate of deacylation of N-acyl derivatives of deoxycytidine is faster than that of deoxyadenosine or deoxyguanosine. The hydrolytic lability is also determined by inductive, resonance, and steric effects. For example, in a series of N-acyl nucleosides, N-benzoyl nucleosides are hydrolyzed sixteen times faster than N-(2,4-dimethoxy)benzoyl nucleoside, perhaps due to a combination of inductive and resonance effects.

The choice of a particular N-acyl protecting group also depends on the type of coupling chemistry that is employed. The group should enhance the solubility of the nucleoside in organic solvents so that it can be adapted for the desired coupling reaction. When phosphodiester and phosphotriester chemistries are used in oligonucleotide synthesis, it is necessary to select sturdy N-acyl protecting groups that can withstand the harsh reagents and conditions employed during synthesis. The benzoyl group is sufficient for adenine and cytosine, and the isobutyryl group for guanine. See, Iyer, *Current Protocols in Nucleic Acid Chemistry*, 2.1.7–2.1.9 (2000), the disclosure of which is incorporated by reference herein.

Activating agents that are amenable to the present invention include those that are typically used in the practice of peptide synthesis. See, e.g. Bodanszky and Bodanszky, *The Practice of Peptide Synthesis*, 97–107, (2d. ed. 1994), the disclosure of which is herein incorporated by reference. Activating agents include, among others, O-nitrophenol, 2,4-dinitrophenol, 2,4,5-trichlorophenol, pentachlorophenol, N-hydroxyphthalimide, N-hydroxysuccinimide, hydroxypiperidine, 5-chloro-8-hydroxy-quinoline, and compounds having one of the following formulae:

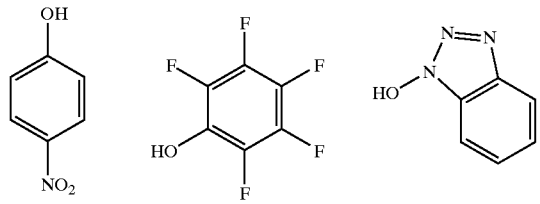

-continued

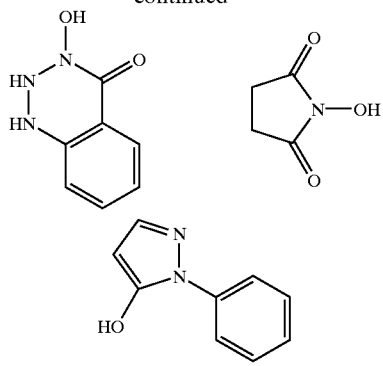

Coupling agents that are amenable to the present invention are generally known in the art and include DCC, diisopropylcarbodiimide, 1-isobutyloxycarbonyl-2-isobutyloxy-1,2-dihydroquinoline (IIDQ), carbonyldiimidazole, N-ethyl-5-phenylisoxazolium-3'-sulfonate (Woodward's Reagent K), O-benzotriazolyl-tetramethyluronium hexafluorophosphate, and 1-benzotriazolyl-tri-dimethylaminophosphonium hexafluorophosphate (BOP-Reagent), and polymer bound coupling agents, such as PS-carbodiimide (Argonaut Technologies), N-cyclohexylcarbodiimide-N'-methyl polystyrene (Novabiochem) and the quaternary carbodiimide resin P-EDC as described by Desai, M. C. and Stramiello, S. L. M. Tet. Letts. 1972, 13, 3281), the disclosure of which is herein incorporatated by reference.

The nucleosides of the present invention include naturally and non-naturally occurring nucleosides. As used herein, the term "nucleoside" refers to a sugar and a nucleobase that are joined together, normally about an "anomeric" carbon on the sugar. Non-naturally occurring nucleosides and nucleotides may be modified by replacing the sugar moiety with an alternative structure having primary and secondary alcohol groups similar to those of ribose. Non-naturally occurring sugars and nucleosidic bases are typically structurally distinguishable from, yet functionally interchangeable with, naturally occurring sugars (e.g. ribose and deoxyribose) and nucleosidic bases (e.g., adenine, guanine, cytosine, thymine). Thus, non-naturally occurring nucleobases and sugars include all such structures which mimic the structure and/or function of naturally occurring species, and which aid in the binding of the oligonucleotide to a target, or which otherwise advantageously contribute to the properties of the oligonucleotide.

A heterocyclic base moiety (often referred to in the art simply as a "base" or a "nucleobase") amenable to the present invention includes both naturally and non-naturally occurring nucleobases. The heterocyclic base moiety further may be protected wherein one or more functionalities of the base bears a protecting group. As used herein, "unmodified" or "natural" nucleobases include the purine bases adenine and guanine, and the pyrimidine bases thymine, cytosine and uracil. Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-aza uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the Concise Encyclopedia Of Polymer Science And Engineering, pages 858–859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289–302, Crooke, S. T. and Lebleu, B., ed., CRC Press, 1993.

Certain heterocyclic base moieties are particularly useful for increasing the binding affinity of the oligomeric compounds of the invention to complementary targets. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Id., pages 276–278) and are presently preferred base substitutions, even more particularly when combined with selected 2'-sugar modifications such as 2'-methoxyethyl groups.

Representative United States patents that teach the preparation of heterocyclic base moieties (modified nucleobases) include, but are not limited to, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, certain of which are commonly owned, and each of which is herein incorporated by reference, and commonly owned U.S. patent application Ser. No. 08/762,587, filed on Dec. 10, 1996, now U.S. Pat. No. 5,808,027, also herein incorporated by reference.

A representative list of 2'-substituent groups amenable to the present invention include $C_1$–$C_{20}$ alkyl, $C_2$–$C_{20}$ alkenyl, $C_2$–$C_{20}$ alkynyl, $C_5$–$C_{20}$ aryl, O-alkyl, O-alkenyl, O-alkynyl, O-alkylamino, O-alkylalkoxy, O-alkylaminoalkyl, O-alkyl imidazole, S-alkenyl, S-alkynyl, NH-alkyl, NH-alkenyl, NH-alkynyl, N-dialkyl, O-aryl, S-aryl, NH-aryl, O-aralkyl, S-aralkyl, NH-aralkyl, N-phthalimido, halogen (particularly fluoro), keto, carboxyl, nitro, nitroso, nitrile, trifluoromethyl, trifluoromethoxy, imidazole, azido, hydrazino, hydroxylamino, isocyanato, sulfoxide, sulfone, sulfide, disulfide, silyl, heterocycle, carbocycle, polyamine, polyamide, polyalkylene glycol, and polyethers of the formula (O-alkyl)$_m$, where m is 1 to about 10. Preferred among these polyethers are linear and cyclic polyethylene glycols (PEGs), and (PEG)-containing groups, such as crown ethers and those which are disclosed by Ouchi et al. (Drug Design and Discovery 1992, 9, 93), Ravasio et al. (J. Org. Chem. 1991, 56, 4329) and Delgardo et. al. (Critical Reviews in Therapeutic Drug Carrier Systems 1992, 9, 249), each of which is herein incorporated by reference in its entirety. Further sugar modifications are disclosed in Cook, P. D., Anti-Cancer Drug Design, 1991, 6, 585–607. Fluoro, O-alkyl, O-alkylamino, O-alkyl imidazole, O-alkylaminoalkyl, and alkyl amino substitution is described in U.S. patent application Ser. No. 08/398,901, filed Mar. 6, 1995, now U.S. Pat. No. 6,866,197 entitled Oligomeric Compounds having Pyrimidine Nucleotide(s) with 2' and 5' Substitutions, hereby incorporated by reference in its entirety.

Additional substituent groups amenable to the present invention include —SR and —NR$_2$ groups, wherein each R is, independently, hydrogen, a protecting group or substituted or unsubstituted alkyl, alkenyl, or alkynyl. 2'-SR nucleosides are disclosed in U.S. Pat. No. 5,670,633, issued Sep. 23, 1997, hereby incorporated by reference in its entirety. The incorporation of 2'-SR monomer synthons are disclosed by Hamm et al., *J. Org. Chem.,* 1997, 62, 3415–3420. 2'-$NR_2$ nucleosides are disclosed by Goettingen, M., *J. Org. Chem.,* 1996, 61, 73–6281; and Polushin et al., *Tetrahedron Lett.,* 1996, 37, 3227–3230.

Further substituent groups have one of formula I or II:

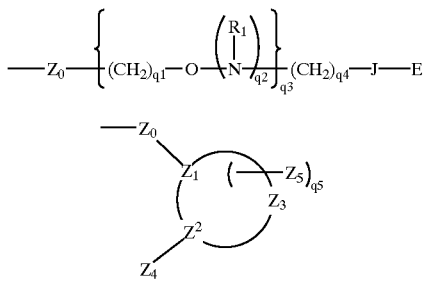

wherein:
$Z_0$ is O, S or NH;
J is a single bond, O or C(=O);
E is $C_1$–$C_{10}$ alkyl, $N(R_1)(R_2)$, $N(R_1)(R_5)$, $N=C(R_1)(R_2)$, $N=C(R_1)(R_5)$ or has one of formula III or IV;

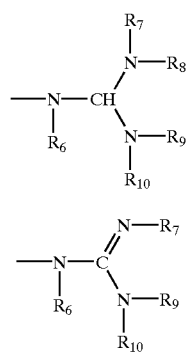

each $R_6$, $R_7$, $R_8$, $R_9$ and $R_{10}$ is, independently, hydrogen, $C(O)R_{11}$, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, $R_7$ and $R_8$, together form a phthalimido moiety with the nitrogen atom to which they are attached;

or optionally, $R_9$ and $R_{10}$, together form a phthalimido moiety with the nitrogen atom to which they are attached;

each $R_{11}$ is, independently, substituted or unsubstituted $C_1$–$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;

$R_5$ is T—L,
T is a bond or a linking moiety;
L is a chemical functional group, a conjugate group or a solid support material;
each $R_1$ and $R_2$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein said substitution is $OR_3$, $SR_3$, $NH_3^+$, $N(R_3)(R_4)$, guanidino or acyl where said acyl is an acid amide or an ester;

or $R_1$ and $R_2$, together, are a nitrogen protecting group or are joined in a ring structure that optionally includes an additional heteroatom selected from N and O;

or $R_1$, T and L, together, are a chemical functional group;
each $R_3$ and $R_4$ is, independently, H, $C_1$–$C_{10}$ alkyl, a nitrogen protecting group, or $R_3$ and $R_4$, together, are a nitrogen protecting group;

or $R_3$ and $R_4$ are joined in a ring structure that optionally includes an additional heteroatom selected from N and O;

$Z_4$ is OX, SX, or $N(X)_2$;
each X is, independently, H, $C_1$–$C_8$ alkyl, $C_1$–$C_8$ haloalkyl, C(=NH)N(H)$R_5$, C(=O)N(H)$R_5$ or OC(=O)N(H)$R_5$;

$R_5$ is H or $C_1$–$C_8$ alkyl;
$Z_1$, $Z_2$ and $Z_3$ comprise a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic, or saturated or unsaturated heterocyclic;

$Z_5$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_1)(R_2)$ $OR_1$, halo, $SR_1$ or CN;

each $q_1$ is, independently, an integer from 1 to 10;
each $q_2$ is, independently, 0 or 1;
$q_3$ is 0 or an integer from 1 to 10;
$q_4$ is an integer from 1 to 10;
$q_5$ is from 0, 1 or 2; and
provided that when $q_3$ is 0, $q_4$ is greater than 1.

Representative substituent groups of Formula I are disclosed in U.S. patent application Ser. No. 09/130,973, filed Aug. 7, 1998, now U.S. Pat. No. 6,172,209 entitled "Capped 2'-Oxyethoxy Oligonucleotides," hereby incorporated by reference in its entirety.

Representative cyclic substituent groups of Formula II are disclosed in U.S. patent application Ser. No. 09/123,108, filed Jul. 27, 1998, now U.S. Pat. No. 6,271,358 entitled "RNA Targeted 2'-Modified Oligonucleotides that are Conformationally Preorganized," hereby incorporated by reference in its entirety.

Particularly preferred substituent groups include $O[(CH_2)_nO]_mCH_3$, $O(CH_2)_nOCH_3$, $O(CH_2)_nNH_2$, $O(CH_2)_nCH_3$, $O(CH_2)_nONH_2$, $O(CH_2)_nON[(CH_2)_nCH_3)]_2$ (where n and m are from 1 to about 10), $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino and substituted silyl. Another particularly preferred modification includes 2'-methoxyethoxy (2'O—CH$_2$CH$_2$OCH$_3$ or 2'-MOE, Martin et al., *Helv. Chim. Acta,* 1995, 78, 486). A further preferred substituent group is 2'-dimethylaminooxyethoxy, i.e., a O(CH$_2$)$_2$ON(CH$_3$)$_2$ group, also known as 2'-DMAOE. Representative aminooxy substituent groups are described in co-owned U.S. patent application Ser. No. 09/344,260, filed Jun. 25, 1999, entitled "Aminooxy-Functionalized Oligomers"; and U.S. patent application Ser. No. 09/370,541, filed Aug. 9, 1999, also identified by entitled Aminooxy-Functionalized Oligomers and Methods for Making Same; hereby incorporated by reference in their entirety.

Other preferred modifications include 2'-methoxy (2'-O—CH$_3$), 2'-aminopropoxy (2'OCH$_2$CH$_2$CH$_2$NH$_2$) and 2'-fluoro (2'-F). The configuration of the substituent group is also variable such as at the 2'-position. In addition to the ribose configuration, the arabinose configuration is also amenable to the present invention. Arabinose modifications are known to those skilled in the art and include more recent procedures described in for example, Damha et. al., *J.A.C.S.,* 1998, 120, 12976–12977; *Bioconjugate Chem.,* 1999, 10, 299–305; Nucleic Acids Res. (2000), 28(18), 3625–3635; Biochemistry (2000), 39(24), 7050–7062.

Similar modifications may also be made at other positions on nucleosides and oligomers, particularly the 3' position of the sugar on the 3' terminal nucleoside or at a 3'position of a nucleoside that has a linkage from the 2'-position such as a 2'–5' linked oligomer and at the 5'-position at a 5'-terminus. Oligomers may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920, certain of which are commonly owned, and each of which is herein incorporated by reference, and commonly owned U.S. Pat. No. 5,859,221, also herein incorporated by reference.

Representative guanidino substituent groups that are shown in formula III and IV are disclosed in co-owned U.S. patent application Ser. No. 09/349,040, entitled "Functionalized Oligomers", filed Jul. 7, 1999, hereby incorporated by reference in its entirety.

Representative acetamido substituent groups are disclosed in U.S. patent application Ser. No. 09/378,568, entitled "2'-O-Acetamido Modified Monomers and Oligomers", filed Aug. 19, 1999, also identified by hereby incorporated by reference in its entirety.

Representative dimethylaminoethyloxyethyl substituent groups are disclosed in International Patent Application PCT/US99/17895, entitled "2'-O-Dimethylaminoethyloxyethyl-Modified Oligonucleotides", filed Aug. 6, 1999, also identified by hereby incorporated by reference in its entirety.

As will be recognized additional objects, advantages, and novel features of this invention will become apparent to those skilled in the art upon examination of the following examples thereof, which are not intended to be limiting.

Experimental

General

The nucleosides, benzoic acid, phenoxyacetic acid and isobutyric acid were purchased from Aldrich Chemical Co. DCC was purchased from Sigma Chemical Co. USA. The polymer bound DCC 'PS-carbodiimide' was purchased from Argonaut Technologies. All the solvents used were purified and duly dried before use. UV spectra were recorded on 220S Hitachi spectrophotometer. $^1$H NMR spectra were recorded on Bruker DRX 300. Small amounts of all the three new derivatives [Scheme 1, (A), (B) & (C)] were hydrolyzed to get the starting nucleosides for confirmation of their structures.

Because dicyclohexylcarbodiimide is a hazardous chemical, it was not used as a powder. After weighing, it was melted in a sealed tube (m.p. 35° C.) and then poured into the reaction mixture. See, methods described by Pon, *Protocols for Oligonucleotides and Analogs;* Agarwal Ed., Humana Press, Totowa, N.J. (2000) Methods in Molecular Biology vol. 20, Chapter 19, p. 473.

General Method for N-acylation of Deoxyadenosine and Adenosine (See FIG. 1)

A sample of dried benzoic acid or phenoxyacetic acid (1 mmol) was dissolved in dry dioxane (10 ml). This mixture was stirred while a solution of p-nitrophenol (1.2 mmol) in dry dioxane was added. After 10 min. of stirring dicyclohexylcarbodiimide (DCC) (1.25 mmol) was added. The reaction mixture was allowed to stir at room temperature for 2 hrs. Completion of the reaction was assessed by the absence of the starting material on TLC. The reaction mixture was cooled to 0° C. in an ice-bath and deoxyadenosine (1 mmol) dissolved in 5 ml of pyridine was gradually added to it. After 10 min. DCC (1.25 mmol) was again added and the raw material was allowed to stir for 2 hrs. The reaction mixture was filtered to remove precipitated DCU and then evaporated to a gum in vacuo. It was then poured in 5% aq. NaHCO$_3$ solution and extracted with dichloromethane (4×5 ml). The organic layer was washed with water to remove released p-nitrophenol until the water became colorless and then dried over Na$_2$SO$_4$, filtered and evaporated to dryness. The residue was extracted in diethyl ether and kept for crystallisation. Data obtained are tabulated in Table 3 below.

TABLE 3

| Compound | Yield | Rf$_{(2)}$ | UV$_{(MeOH)}$ | IR$_{(KBr)}$ | $^1$H NMR(CDCl$_3$/CD$_3$OD) |
|---|---|---|---|---|---|
| N$^6$-Bz-dA | 81% | 0.56 | 260, 310, 390 | 3500–3400(S, B), 1750(S) 1352(M), 782(W) | 8.59(H8, s), 8.33(H2, s), 8.0–7.8 (benzoyl, 2H, m) 7.5–7.3 (benzoyl, 3H, m), 6.08(H$_1$, d, J 6.0 Hz) |
| N$^6$-phenoxyacetyl-dA | 62% | 0.53 | 285 | 3482–3390(S, B), 1760(S) 1335(M), 776(W) | 12.7(N—H, broad, s), 7.87(H8, s), 7.5–7.0 (phenoxyacetyl, 5H, m), 5.98(H1, s), 4.81(phenoxyacetyl, 2H, s). |
| N$^2$-isobutyryl-dG | 82% | 0.56 | 282 | 3485–3385(S, B), 1765(S) 1340(M), 782(W) | 12.3(N—H; broad, s), 11.85(N—H, broad, s), 7.81 (H8, s), 2.5(s, 2H), 1.25(d, 6H) |

TABLE 3-continued

| Compound | Yield | Rf$_{(2)}$ | UV$_{(MeOH)}$ | IR$_{(KBr)}$ | $^1$H NMR(CDCl$_3$/CD$_3$OD) |
|---|---|---|---|---|---|
| N$^6$-Bz-A | 78% | 0.60 | 262, 310, 390 | 3500–3400(S, B), 1750(S), 1355(M), 784(W) | 8.70(H8, s), 8.32(H2, s), 8.0–7.8(benzoyl, 2H, m), 7.5–7.3(benzoyl, 3H, m), 6.08(H$_1$, d, J 6.0 Hz) |
| N$^6$-phenoxyacetyl-A | 77% | 0.62 | 286 | 3490–3380(S, B), 1760(S), 1355(M), 786(W) | 12.75(N—H, broad, s), (H8, s), (7.5–7.0) (phenoxyacetyl, 5H, m) (H1, s), 4.82(phenoxyacetyl, 2H, s) |
| N$^2$- Isobutyryl-G | 84% | 0.55 | 291 | 3485–3382(S, B), 1776(S), 1350(M), 785(W) | 12.21(N—H, broad, s), 11.87(N—H, broad, s) 7.81(H$_8$, s), 2.8(s, 2H), 1.25(d, 6H) |

General Method for N-acylation of Deoxyguanosine and Guanosine

Above described method was repeated by taking isobutyric acid in place of benzoic acid with deoxyguanosine. Data is assembled in Table 3.

General Method for Preparation of 5'-O-dimethoxytrityl-N-acyl-2'-deoxynucleosides and Nucleosides Each N-acylated 2'-deoxynucleoside, i.e. N$^6$-benzoyl-dA, N$^6$-phenoxyacetyl-dA and N$^2$-isobutyryl-dG, (1 mmol) was treated with 4,4'-dimethoxy trityl chloride (1.2 mmol) in pyridine (10 ml) in the presence of 4-dimethylaminopyridine (0.12 mmol) as a catalyst at room temperature (25° C.). The completion of the reaction was checked on TLC and the clear solution obtained was evaporated to a gum in vaccuo and further worked by the usual procedure. Gait, *Oligonucleotide Synthesis, A Practical Approach*, 1984, IRL Press Oxford, Washington D.C. Results are tabulated in Table 4 below.

TABLE 4

| Derivatives | Reaction time | Yield | Rf (a) | λ max (nm) |
|---|---|---|---|---|
| 5'-O-DMTr-N$^6$-Bz-dA | 2.0 | 90% | 0.75 | 285 |
| 5'-O-DMTr-N$^6$-phenoxyacetyl-dA | 2.0 | 92% | 0.75 | 286 |
| 5'-O-DMTr-N$^2$-isobutyryl-dG | 2.5 | 85% | 0.68 | 288 |
| 5'-O-DMTr-N$^6$-Bz-A | 2.0 | 86% | 0.75 | 285 |
| 5'-O-DMTr-N$^2$-isobutyryl-G | 2.5 | 88% | 0.70 | 291 |
| 5'-O-DMTr-N$^6$-phenylacetyl-A | 2.0 | 88% | 0.76 | 288 |

(a) (solvent: CH$_2$Cl$_2$/CH$_3$OH 9.8:0.2 v/v)

General Method for N-acylation Using PS-carbodiimide (PS-DCC)

The respective acids (1 mmol) were dissolved in 10 ml of dry dioxane and PS-carbodiimide (1.25 mmol) was added. A solution of p-nitrophenol was added while stirring through a syringe over 0.5 hr. The reaction mixture was allowed to stir at room temperature for 2 hr and then transferred in an ice bath to keep the temperature at 0° C. A solution of deoxynucleoside dissolved in pyridine was added to it via a syringe. After 2 h of stirring, reaction completion was checked on TLC. No starting material was detected. The reaction mixture was then filtered to remove the polymer bound cyclohexylurea (PS-DCU), evaporated to a gum, and poured into a 5% aq. NaHCO$_3$ solution. This was then extracted with DCM (4×5 ml). The organic layer was washed with water, dried over Na$_2$SO$_4$ and filtered. The combined DCM solutions were concentrated to a minimum and then crystallized in ether.

Procedure for Regeneration of PS-Carbodiimide (PS-DCC)

Method A: The polymer bound cyclohexylurea (PS-DCU; 1 g of 1.25 mmol/g) recovered after N-acylation is suspended in dichloromethane (20 ml) in a two-necked round-bottom flask (100 ml) equipped with a silicone rubber septum and a reverse filter funnel under exclusion of moisture and air. Phosphorus oxychloride (POCl$_3$; 0.38 g, 2.5 mmol) is added slowly over a period of 10 minutes to the above suspension of PS-DCU. The mixture is shaken gently for 4–6 hours and supernatant is removed by reverse filtration and replaced by 10% aqueous NaOH (5 ml) and fresh dichloromethane (20 ml). The suspension is shaken for 1 hour and supernatant is removed. The polymer is washed with tetrahydrofuran (2×25 ml) to remove excess of water and base and dried under vacuum to furnish PS-DCC. The process of dehydration is monitored by taking a small amount of POCl$_3$ treated polymer and using it for the conversion of acetic acid to acetic anhydride. The formation of acetic anhydride is monitored by quantitative 1H NMR and GC analysis of the product. The regenerated PS-DCC is found to be stable at room temperature and useful for another round of N-acylation.

Method B: The polymer bound cyclohexylurea (PS-DCU; 1 g of 1.25 mmol/g) recovered after N-acylation is suspended in dimethylformamide (DMF; 10 ml) in a two-necked round-bottom flask (50 ml) equipped with a silicone rubber septum and a reverse filter funnel under exclusion of moisture and air. Tosyl chloride (TsCl; 0.47 g, 2.5 mmol) is added slowly over a period of 20 minutes to the above suspension of PS-DCU. The mixture is shaken gently for 8–10 hours and supernatant is removed by reverse filtration and replaced by 10% aqueous NaOH (5 ml) and tetrahydrofuran (20 ml). The suspension is shaken for 1 hour and supernatant is removed. The polymer is washed with tetrahydrofuran (2×25 ml) to remove excess of water, DMF and base and dried under vacuum to furnish PS-DCC.

Compatible solvents: All solvents that swell polystyrene can be used for above reaction. Some other examples are dichloroethane, chloroform, pyridine, NMP, dioxane and others listed in Organic Synthesis on Solid Phase by F. Z. Dorwald, Wiley-VCH publication 2000, page 15.

Conditions for Deprotection

The removal conditions for all three protecting groups were studied by treating the N-protected nucleosides with 40% ammonia at 25° C., 40° C. and 50° C. Reactions were quenched after 0.5, 1, 2, 3, 4, 5 and 6 h durations. After hydrolysis, the mixtures were analyzed for deprotected 2'-deoxynucleosides on semi-preparative TLC and subsequent estimation by UV. The results were then matched with the same procedure carried out on HPLC. Results were found to be comparable to the authentic sample of N-protected nucleosides.

We claim:

1. A method for selectively protecting an exocyclic amino function of a purine nucleoside comprising:
   contacting an amino protecting reagent with an activating agent in the presence of a coupling agent to form an activated ester; and reacting said activated ester with said purine nucleoside to covalently attach a protecting group to said exocyclic amino function.

2. The method of claim 1 wherein said protecting group is formyl, isobutyryl, methoxyacetyl, allyloxycarbonyl, isopropoxyacetyl, levulinyl, 4-pentenoyl, 4-nitrophenylethyloxycarbonyl, phenylacetyl, 4-(t-butyl)phenyl acetyl, 9-fluorenylmethoxycarbonyl, α-phenylcinnamoyl, phenoxyacetyl, 2-chlorophenoxyacetyl, 2-chloro-4-(tert-butyl) phenoxyacetyl, 4-(t-butyl)phenoxyacetyl, benzoyl, 2-(4-methyl)sulfonylethoxycarbonyl, 2-(4-chloro)sulfonylethoxycarbonyl, 2-(4-nitro)sulfonylethoxycarbonyl, diphenylacetyl, 3,4-dichlorobenzoyl, 3-methoxy4-phenoxybenzoyl, 2-(acetoxylmethyl)benzoyl, benzoyloxymethylbenzoyl, 1,8-naphthaloyl, 2-chlorophenoxyacetyl, or 2-(t-butyldiphenylsilyloxymethyl)benzoyl.

3. The method of claim 2 wherein said protecting group is benzoyl, isobutyryl, or phenoxyacetyl.

4. The method of claim 1 wherein said purine nucleoside comprises an adenine or guanine moiety.

5. The method of claim 1 wherein said activating agent is O-nitrophenol, 2,4-dinitrophenol, 2,4,5-trichlorophenol, pentachlorophenol, N-hydroxyphthalimide, N-hydroxysuccinimide, hydroxypiperidine, 5-chloro-8-hydroxy-quinoline, or has one of the following formulae:

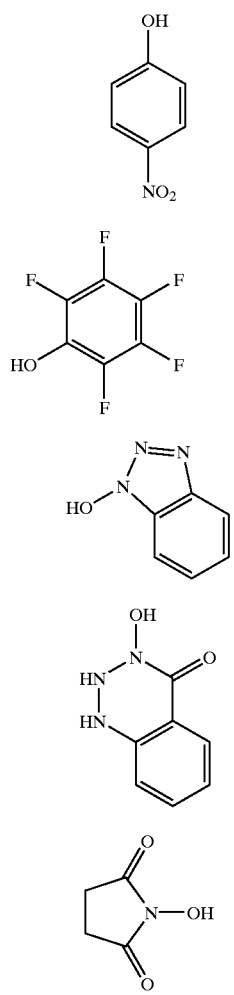

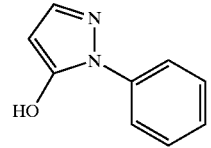

6. The method of claim 1 wherein said purine nucleoside comprises an adenine moiety, said protecting group is benzoyl or phenoxyacetyl, and said activating agent is p-nitrophenol.

7. The method of claim 1 wherein said purine nucleoside comprises a guanine moiety, said protecting group is isobutyryl, and said activating agent in p-nitrophenol.

8. The method of claim 5 wherein said activating agent is p-nitrophenol.

9. A method for selectively protecting an exocyclic amino function of a purine nucleoside comprising:
   contacting an amino protecting reagent with p-nitrophenol in the presence of a coupling agent to form a p-nitrophenyl ester; and
   reacting the ester with said purine nucleoside to covalently attach a protecting group to said exocyclic amino function.

10. The method of claim 9 wherein said protecting group is benzoyl, isobutyryl, or phenoxyacetyl.

11. The method of claim 9 wherein said purine nucleoside comprises an adenine or guanine moiety.

12. A method for selectively protecting an exocyclic amino function of a purine nucleoside comprising:
   contacting a protecting reagent with an activating agent in the presence of a polymer bound coupling agent to form an activated ester;
   reacting the activated ester with said purine nucleoside to covalently attach a protecting group to said exocyclic amino function; and
   filtering the reacted polymer bound coupling agent from the reaction mixture.

13. The method of claim 12 further comprising recycling said reacted polymer bound coupling agent.

14. The method of claim 13 wherein said recycling is effected by dehydrating said reacted polymer bound coupling agent with a dehydrating agent in the presence of an organic solvent.

15. The method of claim 14 wherein said dehydrating agent is tosyl chloride or $POCl_3$.

16. The method of claim 12 wherein said polymer bound coupling agent is N-cyclohexylcarbodiimide-N'-methylpolystyrene.

17. A method for recycling a polymer bound coupling agent comprising dehydrating a reacted polymer bound coupling agent in the presence of an organic solvent.

18. The method of claim 17 wherein said polymer bound coupling agent is N-cyclohexylcarbodiimide-N'-methylpolystyrene.

19. The method of claim 17 wherein said N-cyclohexylcarbodiimide-N'-methylpolystyrene is recycled from its corresponding polymer bound cyclohexylurea by contacting said polymer bound cyclohexyurea with a dehydrating agent in the presence of an organic solvent for a time and under conditions effective to form said N-cyclohexylcarbodiimide.

* * * * *